United States Patent
Sapelnikov et al.

(10) Patent No.: US 7,240,574 B2
(45) Date of Patent: Jul. 10, 2007

(54) SENSORS CARRIER FOR IN-TUBE INSPECTION SCRAPER

(75) Inventors: Uriy A. Sapelnikov, Kolomna (RU);
Boris V. Kozyrev, Kolomna (RU);
Mikhail S. Matveev, Kolomna (RU);
Dmitry G. Chernov, Lukhovitsy (RU);
Vladimir N. Eliseev, Kolomna (RU)

(73) Assignee: Caleste Hills Trading Limited, Nicosia (CY)

( * ) Notice: Subject to any disclaimer, the term of this patent is extended or adjusted under 35 U.S.C. 154(b) by 0 days.

(21) Appl. No.: 10/391,418

(22) Filed: Mar. 18, 2003

(65) Prior Publication Data
US 2003/0183022 A1    Oct. 2, 2003

(30) Foreign Application Priority Data
Mar. 28, 2002   (RU) ............................. 2002107747

(51) Int. Cl.
*G01M 19/00*   (2006.01)
(52) U.S. Cl. .................. 73/865.8; 73/623; 73/40.5 A; 73/40.5 R
(58) Field of Classification Search ............... 73/866.5, 73/623, 865.8, 40.5 R, 40.5 A, 592; 324/220–221
See application file for complete search history.

(56) References Cited

U.S. PATENT DOCUMENTS

| | | | |
|---|---|---|---|
| 3,443,211 A | 5/1969 | Wood et al. | |
| 3,449,662 A | 6/1969 | Wood | |
| 3,496,457 A | 2/1970 | Proctor et al. | |
| 3,529,236 A | 9/1970 | Proctor | |
| 3,539,915 A | 11/1970 | Walters et al. | |
| 3,543,144 A | 11/1970 | Walters et al. | |
| 3,755,908 A | 9/1973 | VerNooy | |
| 3,786,684 A | 1/1974 | Wiers et al. | |
| 3,810,384 A | 5/1974 | Evans | |
| 3,835,374 A | 9/1974 | Frost | |
| 3,940,689 A | 2/1976 | Johnson, Jr. | |
| 3,949,292 A | 4/1976 | Beaver et al. | |
| 3,967,194 A | 6/1976 | Beaver et al. | |
| 3,973,441 A | 8/1976 | Porter | |
| 4,098,126 A | 7/1978 | Howard | |
| 4,153,875 A * | 5/1979 | Pigeon et al. ............... | 324/220 |
| 4,342,225 A | 8/1982 | Jansera et al. | |

(Continued)

FOREIGN PATENT DOCUMENTS

DE         3506622         8/1986

(Continued)

OTHER PUBLICATIONS

Translation of jp49336.*

(Continued)

*Primary Examiner*—Hezron Williams
*Assistant Examiner*—Nashmiya Fayyaz
(74) *Attorney, Agent, or Firm*—Quarles & Brady LLP (57) ABSTRACT

A sensor carrier for an in-tube inspection scraper has setting places for installation of monitoring sensors responsive to any diagnostic parameters of a pipeline being inspected. The carrier includes a set of kinematically interconnected sensor supports that are subjected to an elastic force in the radial direction from the carrier axis. The supports are made as elastic ring-shaped elements or as rows of interconnected elements adjoining the pipe wall or are fixed on elastic components such as rings or sectors of sleeves, and/or are connected to a housing capable of bending. Installed on the supports between the sensors and the internal surface of the pipeline are elastic gaskets. The carrier allows one to increase the efficiency of the flaw detection in pipelines having defects of geometry in the cross section.

32 Claims, 5 Drawing Sheets

U.S. PATENT DOCUMENTS

| | | | |
|---|---|---|---|
| 4,402,213 A * | 9/1983 | Hogan | 73/40.5 R |
| 4,457,073 A | 7/1984 | Payne | |
| 4,598,250 A | 7/1986 | Lorenzi et al. | |
| 4,717,875 A | 1/1988 | Lara | |
| 4,807,484 A | 2/1989 | Goedecke | |
| 4,910,877 A | 3/1990 | Sokol | |
| 4,945,306 A | 7/1990 | Lowther | |
| 4,953,412 A | 9/1990 | Rosenberg et al. | |
| 5,115,196 A | 5/1992 | Low et al. | |
| 5,398,560 A * | 3/1995 | Zollingger et al. | 73/865.8 |
| 5,460,046 A | 10/1995 | Maltby et al. | |
| 5,675,084 A * | 10/1997 | Goedecke | 73/623 |
| 6,848,313 B2 * | 2/2005 | Krieg et al. | 73/623 |

FOREIGN PATENT DOCUMENTS

| | | |
|---|---|---|
| DE | 3706660 | 9/1988 |
| DE | 3719492 | 12/1988 |
| DE | 19747551 | 4/1999 |
| GB | 939172 | 10/1963 |
| GB | 2020023 | 11/1979 |
| JP | 07049336 A * | 2/1995 |
| RU | 2139468 | 10/1999 |
| RU | 2139469 | 10/1999 |
| SU | 1157443 | 5/1985 |

OTHER PUBLICATIONS

English Language Abstract for DE3506622.
English Language Abstract for DE3706660.
English Language Abstract for DE3719492.
English Language Abstract for DE19747551.
English Language Abstract for RU2139468.
English Language Abstract for RU2139469.

* cited by examiner

SENSORS CARRIER FOR IN-TUBE INSPECTION SCRAPER

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

1. Field of the Invention

The invention relates to devices used for flaw detection of long-distance pipelines, mainly oil and gas pipelines through non-destructive methods by passing inside the pipeline an intelligent scraper with monitoring sensors mounted thereon and responding to any diagnostic parameter of the pipeline. The invention primarily relates to means for attaching sensors and maintenance of their necessary spatial location with respect to the pipeline surface during the travel of the scraper.

2. Description of the Related Art

Known in the art are sensor carriers (see GB939172, U.S. Pat. Nos. 3,496,457, 3,449,662, 3,810,384, 3,835,374, 3,940,689, 3,949,292, 3,967,194, 3,973,441, GB2020023, U.S. Pat. Nos. 4,342,225, 4,457,073, 1,157,443, 4,717,875, 4,598,250, DE3506622, DE3706660, U.S. Pat. No. 4,910,877, 4,945,306, 4,953,412, 5,115,196, 3,755,908, 5,460,046, DE19747551, DE3719492) for an in-tube scraper with sites for sensors which are arranged on a surface with axial symmetry (inscribed into a surface with axial symmetry). The carriers are characterized in that they include housing and sensor supports. The use of the above devices does not allow one to obtain a resolution sufficient for identification of defects such as pinpoint corrosion or cracks in the pipeline wall.

Also known in the art are sensor carriers (see U.S. Pat. Nos. 3,529,236, 3,543,144, 3,786,684, RU2139469, RU2139468) for an in-tube inspection scraper with setting places for sensors which are arranged on a surface with axial symmetry (inscribed into a surface with axial symmetry). The carrier is characterized in that it includes a housing and one or several belts of sensor supports spring-loaded in the radial directions and secured on the housing with the help of pivot joints. Each support has setting places for sensors. The advantage of such a sensor carrier is that it allows one to scan the whole surface of the pipeline with overlapping the zones monitored by individual sensors. The main disadvantage of such a carrier is that when it passes a pipeline section with a defect of geometry, for example, a dent, the sensor supports behave as rigid elements, and a knock of the front part of the support against a dent (projection on the pipeline internal surface) is accompanied by a departure of whole support from the non-deformed part of the pipeline. An increase of the distance between the sensors and the internal surface of the pipeline imparts the efficiency of the sensors, and such sections of the pipeline with defect of geometry remain to be not inspected.

Known in the art is a sensor carrier (see U.S. Pat. No. 4,098,126) for an in-tube inspection scraper with setting places for sensors, which are provided on a surface with axial symmetry. The carrier is characterized in that it includes an elastic sleeve whose diameter is less than the pipeline bore diameter, the sensors are installed along the periphery of the sleeve and said sensors are inscribed in a cylinder whose diameter exceeds the sleeve diameter. Such a carrier is advantageous in that, when the scraper travels along a pipeline section with an insignificant defect of geometry, like a dent, the sensors adjoin the deformed surface of the pipeline. The basic disadvantage of such a carrier is that the carrier sensors are arranged as a single belt, and since some distance separates the sensors from each other, this distance restricts the linear resolution of the inspection scraper with such a carrier. Furthermore, the distance between the adjacent sensors cannot be less than the sensor size/and this also restricts the linear resolution. Besides, when the carrier passes pipeline sections having major defects of the geometry in the cross section, the sensors move away from the non-deformed part of the pipeline near the defect of geometry and this is followed by a collapse of the sleeve with sensors. When testing the pipeline consisting of pipes having essentially different thickness of the pipe walls, for example, in the presence of earlier repaired pipeline sections, on the sections with an increased wall thickness, as well as in the presence of a fixed foreign object on the internal pipe surface, the movement of the sensor carrier can be accompanied by a collapse of the sleeve and a loss of orientation of some sensors. Besides, installation of the sensors outside results in a damage of the sensors by such obstacles as jar washers.

A related device for the claimed group of inventions is a known sensor carrier (see U.S. Pat. Nos. 4,807,484 and its equivalents CA1307129, DE3626646, EP0255619, ES2026869, NO172956, NO873252) for an in-tube inspection scraper with setting places for sensors which are arranged on a surface with axial symmetry. The carrier is made as an elastic cylindrical sleeve with protuberances forming a cylinder whose diameter is larger than the internal diameter of the pipe; the sensors are located in the depressions of the sleeve, the protuberances and depressions being oriented under an acute angle to the sleeve axis.

This carrier is advantageous in that the sensors installed along the lines oriented at an angle to the carrier axis allow one to scan the entire surface of the pipeline with overlapping of the zones monitored by individual sensors; the installation of the sensors in the sleeve depressions protects them against damage on such obstacles as jar washers; when passing the pipeline section with a defect of geometry such as a dent, the sensors adjoin the deformed and non-deformed surfaces of the pipeline both along the axis and along the perimeter of the pipeline.

The disadvantage of such a carrier is that the elastic sleeve carrying a large number of sensors with associated cables (which provide high linear resolution) or utilization of heavy sensors (for example, magnetic) with long length and low thickness of the sleeve and, respectively, good elasticity, results in deformation of the elastic sleeve under the total weight of the sensors and cables. This leads to a formation of a gap between the sensors at the top part of the elastic sleeve and the internal surface of the pipeline, in which case the presence of a gap interferes with uniform pressure of the sleeve to the internal wall of the pipe when filling the starting chamber with fluid to be conveyed. The increase of the sleeve rigidity (to avoid the above phenomenon) is accompanied by a loss of elasticity of the sleeve when enveloping the defects of geometry of the pipeline and formation of gaps between the sensors and the internal surface of the pipeline near the defect.

Besides, the gaps between the sensors and the internal surface of the pipeline are also formed when enveloping the defects of geometry by the sensors arranged at the front wall of the sleeve whose ability of compressing in the plane passing through an carrier axis is much lower than at the section of the sleeve remote from its front wall.

SUMMARY OF THE INVENTION

In the claimed group of the inventions for all embodiments of the group (including the first embodiment) there is claimed a sensor carrier for an in-tube inspection scraper with setting places for sensors, which are arranged on a surface with axial symmetry (inscribed into a surface with axial symmetry).

In contrast to the known prior art, the claimed carrier according to the first embodiment of the group of inventions is characterized in that: the carrier includes a plurality of interconnected ring-shaped sensor supports, the setting places for sensors are kinematically interconnected elements of the ring-shaped supports, said elements being subjected to an elastic force in a radial direction from the carrier axis.

The basic technical result (common for all embodiments of the group) obtained as a result of realization of the claimed group of inventions is a higher efficiency of the flaw detection of the pipelines having defects of geometry in the cross section. For all the embodiments of the group the positive result is achieved due to the multiplicity of the elements (supports) with setting places for sensors and separation of the functions of pressing the sensors to the internal surface of the pipeline and enveloping the defects of geometry in the pipe cross section.

The means for achieving said technical result (for the first embodiment) is that the pressure of the elements to the pipe wall is determined by the elasticity of the elements of each support irrespective of the elements of the next support, therefore, departure of the sensor from the internal surface of the pipeline is practically the same also when passing the defect of geometry. The functions of pressure on the sensors and enveloping the obstacles are separated, the ring-shaped supports can provide a sufficient pressure force, and the enveloping is achieved due to the multiplicity of supports whose peripheral parts are subject to deformation irrespective of the adjacent ring-shaped supports.

The development of the first embodiment of a group of inventions is based on the fact that: the external surfaces of the ring-shaped supports extend along the cylindrical surface corresponding to the internal surface of the pipeline, the setting places for sensors are made in the convex parts of the supports and form rows oriented at an angle of 0 to 30 degrees to the carrier axis along a spiral line about the carrier axis; the elements of the ring-shaped support with setting places for sensors are elastically connected to the adjacent elements of the same ring-shaped support with setting places for sensors.

The carrier includes at least four ring-shaped supports, the distance between the adjacent ring-shaped supports not exceeding a half the diameter of the cylinder, into which the sensor support is inscribed; the width of the ring-shaped support (along the carrier axis) is much less than said diameter and makes not more than 0.25 said diameter.

The inspection of the pipeline along the whole perimeter requires a significant number of high-resolution sensors, and their position on the supports with said interval make up a carrier of a small length that reduces disorientation of the sensors on the pipe turns and simplifies the reeving of the inspection scraper with the carrier. The execution of the support with a width within said limits is most preferable for enveloping the pipe geometry defects and free pass of the carrier through the turns and narrowing section of the pipe.

The angle between the direction of the axis of the ring-shaped support and the direction the pipeline axis is within 0 to 30 degrees.

The setting places for sensors are made as holes or cuts or depressions, the amount of setting places (holes or depressions) for the sensors on one ring-shaped support makes 0.3 to 10 cylinder diameters expressed in inches, into which said support is inscribed.

In a possible embodiment of the invention the carrier includes sensors installed in setting places, said sensors being inscribed into a cylinder whose diameter exceeds the diameter of the cylinder, into which the ring-shaped supports are inscribed. When testing the oil pipelines having a paraffin deposit on the walls, such a design allows one to wash the sensors with a flow of the medium being conveyed; at a smaller diameter of the supports uniform pressure of the elements with sensors to the internal surface of the pipeline is not guaranteed.

In a preferable embodiment the ring-shaped supports are made as corrugated elastic rings whose characteristic features are given below after the description of all embodiments of the group of inventions.

Made in the rings (in the convex parts of the rings) are depressions, or holes, or cuts for installation of the sensors therein and free distribution of an ultrasound or a light (electromagnetic) flow from the sensor (ultrasonic, optical or electromagnetic, respectively) to the pipe wall.

In possible optional embodiments: the ring-shaped support comprises rigid links, as well as elastic and/or pivot joints between the links; the ring-shaped support includes rigid and/or elastic links and pivot joints between the links; the ring-shaped support is inscribed into the cylinder whose diameter is less than the internal diameter of the pipeline, but at least equal to a half the diameter of the cylinder, in which the carrier is inscribed; the ring-shaped supports connected in series form a spiral line about the carrier axis; the ring-shaped supports are installed along a single axis, the support axes coinciding with pipeline axis; the ring-shaped supports are rigidly or elastically connected to the adjacent ring-shaped supports, at least some of the ring-shaped supports being fastened together by rods or slats, which may be rigid or elastic; the carrier includes supporting elements connected to the ring-shaped supports and inscribed into a cylinder whose diameter exceeds the diameter of the cylinder, into which the ring-shaped supports are inscribed; the ring-shaped supports are located between said supporting elements, the latter being made as corrugated elastic rings and/or of elastic sleeves and/or elastic disks.

A choice of the type of attaching the supports to each other and the support design is determined by the carrier size and the type of the tested pipeline (a gas pipeline having dry walls or an oil pipeline, in which the petroleum plays a role of lubricant for the scraper sliding along the wall); at a large diameter of the pipe the rigid links and pivot joints are preferable, at a smaller diameter elastic links and connections are desirable.

In preferable execution of the first embodiment the carrier includes skids installed on the supports, in compliance with the description of the second embodiment given below and/or a housing, on which the supports are installed, in compliance with the description of the third embodiment.

Claimed in the second embodiment of the group of inventions is a sensor carrier for an in-tube inspection scraper with setting places for sensors on a surface with axial symmetry.

In contrast to the common prior art, the claimed carrier of the second embodiment of the group is characterized in that: the carrier includes a set of kinematically connected elements (supports) with setting places for sensors and elastic skids capable of sliding along the internal surface of the pipeline, said skids forming gaskets between the elements with setting places for sensors and the internal surface of the pipeline, said elements with setting places for sensors being subjected to the elastic force in the radial direction from the carrier axis.

The basic technical result (common for all embodiments of the group) obtained as a result of realization of the claimed group of inventions is a higher efficiency of the flaw detection in pipelines having defects of geometry in the cross section. For all embodiments of the group the result is achieved due to multiplicity of elements (supports) with setting places for sensors and separation of the functions of pressure on the sensors to the internal surface of the pipeline and enveloping the defects of geometry in the pipe cross section.

The means for achieving said technical result (for the second embodiment) is that the pressure of the kinematically connected elements to the pipe wall is produced by the elastic force of an element under the skids irrespective of force of pressure of the element under the next skids, and departure of the sensor from the internal surface of the pipeline provided by the gasket in the form of a skid practically does not change when the carrier passes over the defect of geometry. The functions of pressure on the sensors and enveloping the obstacles are separated, and the improved enveloping of the obstacles due to a plurality of gaskets in the form of skids and their elasticity has no effect on the force of pressure of the elements, which in this housing can be high enough.

Besides, in the second embodiment of the group it is possible to protect the sensors from their damage at places of defects of geometry, as well as to reduce the wear of the elements with sensors by replacing the worn out gaskets only.

In the second embodiment of the invention each skid forms a gasket between several kinematically connected elements with setting places for sensors and the internal surface of the pipeline; the skids are secured on elements with setting places for sensors; the skids have through holes and/or cuts in the areas between the setting places for sensors and the internal surface of the pipeline that allows one to mount both magnetic and ultrasonic (optical) sensors, providing free distribution of ultrasound or light (electromagnetic flow) flow from the sensor to the pipe wall.

The skids are oriented along the spiral (screw) and/or ring lines about the carrier axis; the angle between the skid direction and the carrier axis direction is of 0 to 30 degrees; the carrier includes elastic elements capable of depressing said skids and/or elements with setting places for sensors in the radial direction from the carrier axis.

In the preferable embodiment of the invention the skids are elastic polymeric and have a thickness not less than 0.01 and not more than 0.2 diameter of the cylinder, in which the carrier is inscribed, skid width being not less than 0.02 and not more than 0.4 of said diameter.

The given range was found as an optimal one for uniform enveloping of the typical defects of geometry of the pipe, on the one hand, and for avoiding the disorientation of the next elements with sensors, on the other hand.

In a possible realization of the support the skids connected in series form a spiral (helical line) about the carrier axis or the skids form rings and/or ring-shaped assemblies coaxial with the pipeline axis.

In others possible embodiments of the invention: the skid includes rigid links, elastic and/or pivot joints between the links; the skid includes rigid and/or elastic links and pivot joints between the links; the setting places for sensors are made in the form of holes, and/or cuts, and/or depressions and form rows oriented at an angle of 0 to 30 degrees to the carrier axis along the spiral line about the carrier axis, the setting places for sensors being made in convex parts of the elements.

The choice of a type of fastening the supports to each other and their construction are determined by the standard size of the support and by the tested pipeline type: at a large diameter and dry surface of the pipeline rigid couplings and pivot joints are preferable; at a low diameter of the pipeline elastic links and couplings are preferable.

In the preferable embodiment the elements with setting places for sensors are made as corrugated elastic rings, whose features in a preferable embodiment are specified below after the description of all embodiments of the group of inventions.

The amount of setting places for sensors in one ring is 0.3 to 10 diameters of the cylinder expressed in inches, into which said ring is inscribed.

The carrier includes supporting elements connected to the elements with setting places for sensors, the supporting elements are inscribed into the cylinder whose diameter exceeds the diameter of the cylinder, in which the elements with setting places for sensors are inscribed, the elements with setting places for sensors being disposed between said supporting elements. The supporting elements are made as corrugated elastic (polymeric) rings and/or elastic (polymeric) sleeves and/or elastic (polymeric) disks.

In preferable second embodiment of the group of inventions the sensor carrier includes ring-shaped sensor supports, on which are skids installed, in compliance with the above-described first embodiment, and/or the carrier includes a housing, on which there are installed elements with setting places for sensors and/or skids, in compliance with the third embodiment described below, and/or rows of grouped elements, on which skids are installed, in compliance with the fourth embodiment described below, and/or a belts of sensor supports on which sensor supports are installed, in compliance with the further description of the fifth embodiment, and/or sensor supports installed on ring elements, on which skids are installed, in compliance with the sixth embodiment.

For the third embodiment of the group of inventions a sensor carrier is also claimed for an in-tube inspection scraper with setting places for sensors arranged on a surface with axial symmetry.

In contrast to the known prior art, the claimed carrier of the third embodiment of the group is characterized in that: the carrier includes a housing and a set of elements (supports) kinematically connected to the housing, with setting places for sensors, the housing being capable of bending and the elements with setting places for sensors being subjected to an elastic force acting in the radial direction from the carrier axis.

The basic technical result (common for all embodiments of the group) obtained as a result of realization of the claimed group of inventions is a higher efficiency of the flaw detection of the pipelines having defects of geometry in the cross section. For all the embodiments of the group the positive result is achieved due to the multiplicity of the elements (supports) with setting places for sensors and separation of the functions of pressing the sensors to the internal surface of the pipeline and enveloping the defects of geometry in the pipe cross section.

The means for achieving said technical result (for the third embodiment) is that during the passage of the carrier through the pipe section with a defect of geometry the elements with setting places for sensors are kinematically connected with the housing providing (at any length of the carrier) good maneuverability of the carrier in the pipe turns and in the lowering cross sections (including those formed by the defects of the pipe geometry) due to the bending capacity of the housing making it possible to press the elements to the internal surface of the pipeline with a sufficient force irrespective of the location of the element on the housing; the functions of pressure on the sensors and enveloping the obstacles are different.

In the third embodiment of the group of inventions: the housing has an axis of symmetry coinciding with an axis of the pipeline; the elements with setting places for sensors and the housing form elastic and/or pivot joints (by means of hinges); the length of the rigid sections of the housing along the carrier axis does not exceed a half the diameter of the cylinder, into which the carrier is inscribed.

The lower limit of an allowable bending radius of the carrier axis does not exceed three diameters of the cylinder, into which the carrier is inscribed (in the preferable embodiment it is not more than 1.5 diameter).

The length of the rigid section and the bending radius determine the efficiency of smoothing the displacement of the adjacent elements with sensors when the scraper passes the defects of the pipe geometry and bends and detects the flaws of the pipeline using its sensors.

In one optional embodiment the housing includes rigid links, as well as elastic and/or pivot joints between the links.

In another optional embodiment the housing includes rigid and/or elastic links and pivot joints between the links, the elastic links being made of an elastic polymeric material.

In a preferable embodiment the housing is made as a braid, or a cable, or a hose, or bellows, or a spring, or a strip (it includes a braid, or a cable, or a hose, or bellows or a spring or a strip).

The choice the housing design is determined by the standard size of the carrier and by the type of the tested pipeline: at a large diameter and a dry surface of the pipeline rigid couplings and pivot joints are preferable, at a low diameter of the pipeline elastic links and couplings are advisable.

In a preferable embodiment the elements with setting places for sensors are made as corrugated elastic rings whose features in a preferable embodiment are specified below after the description of all embodiments of the group of inventions. The amount of setting places for sensors in one ring is 0.3 to 10 diameters of the cylinder expressed in inches, into which said ring is inscribed.

The carrier includes supporting elements connected to the elements with setting places for sensors; the supporting elements are inscribed into a cylinder whose diameter exceeds the diameter of the cylinder, into which the elements with setting places for sensors are inscribed; the elements with setting places for sensors are located between said supporting elements, the supporting elements being made as corrugated elastic rings (their features in a preferable embodiment are specified below after the description of all embodiments of the group of inventions) and/or elastic sleeves, and/or elastic disks.

The setting places for sensors are made as holes or cuts or depressions and form rows oriented at an angle of 0 to 30 degrees to the carrier axis along the spiral line about the carrier axis, the setting places for sensors being made in the convex parts of the elements.

In the preferable third embodiment the carrier includes ring-shaped sensor supports mounted on a housing in compliance with the above-described first embodiment and/or skids installed on the elements with setting places for sensors in compliance with the above-described second embodiment, and/or rows of grouped elements fastened to the housing in compliance with the fourth embodiment described below, and/or belt of sensor supports fastened to the housing in compliance with the fifth embodiment described below, and/or ring elements mounted on the housing and having sensor supports in compliance with the sixth embodiment of the invention described below.

In the fourth embodiment of the group of inventions there is claimed a sensor carrier for an in-tube inspection scraper having setting places for sensors which are arranged on a surface with axial symmetry.

In contrast to the known prior art, the claimed carrier of the fourth embodiment of the group is characterized in that: the carrier includes interconnected rows of grouped elements (supports) with setting places for sensors; each element of the row is kinematically connected to the next (neighboring) elements of the row, the elements with setting places for sensors being subjected to an elastic force in the radial direction from the carrier axis.

The basic technical result (common for all embodiments of the group) obtained as a result of realization of the claimed group of inventions is a higher efficiency of the flaw detection of the pipelines having defects of geometry in the cross section. For all the embodiments of the group the positive result is achieved due to the multiplicity of the elements (supports) with setting places for sensors and separation of the functions of pressing the sensors to the internal surface of the pipeline and enveloping the defects of geometry in the pipe cross section The mechanism for obtaining said technical result (for the fourth embodiment) consists in that when the carrier travels through a pipe section having a defect of geometry, some of the grouped elements are bending, and the elements with sensors both in the zone of pipe deformation and in the non-deformed zone are pressed to the internal surface of the pipeline, in which case the ability of enveloping the defects of geometry is determined by relative mobility between the adjacent elements in each row irrespective of the elasticity of the material, from which the grouped elements are made; the functions of pressure on the sensors and enveloping the obstacles are different.

In the fourth embodiment: the carrier includes spring-loading members secured to the rows of grouped elements and capable of depressing the grouped elements in the radial direction from the carrier axis; each row of elements is oriented along the spiral and/or annular line about the carrier axis, the row of grouped elements having surfaces capable of sliding along the internal surface of the pipeline.

The orientation of the rows of sensors provides overlapping the zone of action of the sensors in the cross section of the pipeline.

In possible embodiments of the invention: the elements of the row form hinged and/or elastic couplings with the adjacent elements of the same row; the elements of the row form pivot joints with the adjacent elements of the same row, the pivot joints between the adjacent elements of the row being formed by surfaces of elements of the row at of contact with the adjacent elements of the row; the elements of the row form elastic couplings with the adjacent elements of the same row, the elastic couplings between the adjacent elements of the row are formed with the help of elastic elements (plates and/or springs), each of which is fixed at least on two adjacent elements of the row, the elastic elements being capable of depressing the grouped elements in the radial direction from the carrier axis; the adjacent rows of grouped elements form hinged and/or elastic couplings with the other (neighboring) rows, the elements of the row forming hinged and/or elastic couplings with elements of other (neighboring) row; the adjacent rows of grouped elements form pivot joints with the other (neighboring) rows, the elements of the row form pivot joints with the elements of the other (neighboring) row, the pivot joints between the adjacent elements of the different (neighboring) rows are formed by hinged mechanisms; the adjacent rows of grouped elements form elastic couplings with the other (neighboring) rows, the elastic couplings between the different (neighboring) rows are formed with the help of elastic elements, each of which is fixed at least on two adjacent rows, said elastic elements being capable of depressing the grouped elements in the radial direction from the carrier axis; the elements of the row form elastic couplings with elements of the other (neighboring) row, the elastic couplings between the elements of the different rows are formed with the help of elastic elements (plates and/or springs), each of which is fixed at least on two elements relating to different (neighboring) rows, the elastic elements being capable of depressing the grouped elements in the radial direction from the carrier axis.

The carrier includes a housing, rows of grouped elements being connected to the housing with the help of elastic and/or hinged mechanisms.

The choice of a type of attaching the rows to the housing and fixing the elements in the rows depends on the standard size of the carrier and on the type of the tested pipeline: at a large diameter and a dry surface of the pipeline rigid couplings and pivot joints are preferable, at a low diameter of the pipeline elastic links and couplings are preferable.

The carrier includes elastic disk-shaped and/or sleeve supports mounted along an axis coinciding with the carrier axis, the rows of grouped elements being installed on said supports.

The carrier includes ring-shaped elastic supports mounted along an axis coinciding with the carrier axis, the rows of grouped elements being installed on said support; in preferable embodiment the ring-shaped supports are made as corrugated elastic rings whose features in preferable embodiment are specified below after the description of all embodiments of the group of inventions.

The setting places for sensors are made as holes or cuts or depressions and form rows oriented at an angle of 0 to 30 degrees to the carrier axis along the spiral line about the carrier axis, the setting places for sensors being made in the convex parts of the elements.

In the preferable embodiment: each row is formed by elements adjoining each other and strapped by an elastic element capable of bending, the adjacent elements in each row are pressed to each other, said strapping element is made of an elastic polymeric material in the form of a braid or cable, or a tape, or a tube, or bellows, or a spring; the grouped elements being made of wear-resistant (polymeric) material; each elements in the row of grouped elements has centering members, which enable the elements of the row to be centered relative to the adjacent elements; the centering members are made in the form of projections and slots so that the projections of one member enter the slots of the adjacent member, said projections being formed by metal members fixed in the grouped elements, and the centering members forming pivot joints between the adjacent elements of the row.

In the preferable version of the fourth embodiment of the group of inventions the carrier includes elastic rings carrying rows of grouped elements, in compliance with the above-described first embodiment, and/or rows of skids, in compliance with the above-described second embodiment, and/or a carrier housing accommodating rows of grouped elements, in compliance with the above-described third embodiment, and/or spring-loading members carrying rows of grouped elements, in compliance with the description of the fifth embodiment given below, and/or ring elements carrying rows of grouped elements, in compliance with the sixth embodiment described below.

In the fifth embodiment of the group there is also claimed a sensor carrier for an in-tube inspection scraper with setting places for sensors which are arranged on a surface with axial symmetry.

In contrast to the known prior art the claimed carrier on the fifth embodiment of the group is characterized in that: the carrier includes a belt of kinematically interconnected sensor supports with setting places for sensors installed along the perimeter about the carrier axis and spring-loading members attached to the edges of said supports at both sides of the supports relating to the belt plane, said spring-loading members being capable of depressing said supports in a radial direction from the carrier axis.

The basic technical result (common for all embodiments of the group) obtained as a result of realization of the claimed group of inventions is a higher efficiency of the flaw detection of the pipelines having defects of geometry in the cross section. For all the embodiments of the group the positive result is achieved due to the multiplicity of the elements (supports) with setting places for sensors and separation of the functions of pressing the sensors to the internal surface of the pipeline and enveloping the defects of geometry in the pipe cross section.

The mechanism for obtaining said technical result (in the fifth embodiment) consists in that when the carrier travels near the pipe section with a defect of geometry the support (element) envelops the obstacle: at the beginning of movement the front part of the support is closer to the pipeline axis than the rear part, at the end of the enveloping movement the rear part of the support is closer to the pipeline axis than the front one. In so doing the next supports along the perimeter about the carrier axis above the zero-defect pipeline sections do not make similar enveloping movements, and the gap between the sensors installed in these supports and the internal surface of the pipeline practically does not change. In this case, the functions of pressing the sensors to the pipe surface and enveloping the obstacles are separated, and the high pressure force provided by the elastic elements has no effect on the ability of the supports to envelope the obstacles in this way.

The supports or spring-loading members include elastic (polymeric) elements capable of sliding along the internal surface in the zone in front of the setting places for sensors. The elastic elements in front of the sensors allow one to damp the recoil and to smooth the vibration, when the carrier passes an obstacle with a defect in the pipe geometry in the cross section at a sharp angle.

In the fifth embodiment: the supports or spring-loading members include elastic (polymeric) elements capable of sliding along the internal surface of the pipeline in the zone after the setting places for sensors; the elastic elements form pairs on different sides of the setting places, the supports have plats forming gaskets between the setting places for sensors and the internal surface of the pipeline, said gaskets being capable of closing the sensors in the setting places.

The elastic (polymeric) elements after the sensors (along the path of movement of the carrier with a scraper in the pipeline) allow one to damp the recoil and to smooth the vibration when the carrier passes an obstacle in the pipeline at a sharp angle at the end of passing the obstacle.

The belt supports or spring-loading members have gaskets capable of sliding along the internal surface of the pipeline, which have elasticity necessary for smoothing the vibration and wear resistance sufficient for quite a number of the diagnostic travels of the carrier without replacement of the worn out elastic elements or spring-loading members.

The spring-loading members include levers installed at an angle of 30 to 80 degrees to the carrier axis, said levers being made in the form of two belts of radially extending levers at different sides of the support belts; the levers of one belt are installed opposite to the levers of the second belt, the supports are fixed with the peripheral parts of the levers; the carrier includes a housing; the peripheral parts of the levers have integral parts for fixing the supports; the angular width of the lever in its peripheral part relative to the carrier axis (in a plane normal to the support axis) does not exceed 45 degrees.

Such a design provides symmetric depression of the supports from the carrier axis and independent enveloping of obstacles by the supports secured to different levers.

The spring-loading members are made of an elastic polymeric material, an average thickness of the elastic element making 0.02-0.15 diameter of the cylinder, into which the carrier is inscribed, the length of the part of the elastic element capable of bending is equal to 0.05-0.5 said diameter; several supports are attached to one elastic element, the elastic elements being made as sectors of elastic sleeves, said sectors having radial cuts.

These parameters of the spring-loading members provide smoothing the vibrations of the supports, on the one hand, and a sufficient effort of depressing the supports with sensors from the carrier axis, on the other hand.

The carrier includes elastic elements resting on the spring-loading members and depressing them from the carrier axis in the radial direction. Said elastic elements are made as corrugated elastic rings that allow one to choose a material of the levers elastic enough for smoothing the vibration of the supports irrespective of the force required for releasing the supports provided by said elastic elements.

In a possible design of the support the spring-loading members are made as corrugated elastic rings.

The features of the corrugated elastic rings in a preferable embodiment are specified below after the description of all embodiments of the group of inventions.

The setting places for sensors are made as holes or cuts or depressions and form rows oriented at an angle of 0 to 30 degrees to the carrier axis along the spiral line about the carrier axis, the setting places for sensors being made in the convex parts of the supports, and the carrier includes a set of belts of supports.

The length of the support along the carrier axis does not exceed 0.4 diameter of the cylinder, in which the carrier is inscribed, the angular width of the support relating to the carrier axis in a plane normal to the axis of the support does not exceed 45 degrees; a large length of the support weakens the ability of enveloping the defects of geometry in the pipe.

In a preferable version of the fifth embodiment the sensor carrier also includes skids installed on the belt of supports in compliance with the above-described second embodiment and/or a carrier housing, on which the belt of supports is installed, in compliance with the above-described third embodiment, and/or the supports are made as rows of grouped elements in compliance with the above-described fourth embodiment and/or spring-loading members are made as ring elements in compliance with the further description sixth embodiment.

For the sixth embodiment of the group of inventions there is claimed a sensor carrier for an in-tube inspection scraper with setting places for sensors which are arranged on a surface with axial symmetry.

In contrast to the known prior art, the claimed carrier of the sixth embodiment of the group is characterized in that: the carrier includes a set of kinematically interconnected sensor supports (rigid or elastic, polymeric) with setting places for sensors, as well as some elastic ring-shaped elements capable of depressing the supports in the radial direction from the carrier axis, the sensor supports being attached to said elastic ring-shaped elements.

The basic technical result (common for all embodiments of the group) obtained as a result of realization of the claimed group of inventions is a higher efficiency of the flaw detection of the pipelines having defects of geometry in the cross section. For all the embodiments of the group the positive result is achieved due to the multiplicity of the elements (supports) with setting places for sensors and separation of the functions of pressing the sensors to the internal surface of the pipeline and enveloping the defects of geometry in the pipe cross section.

The mechanism for obtaining said technical result (in the sixth embodiment) consists in that the pressure force on the part of the support (element), adjoining the defect of the pipe wall geometry is preset by the elasticity of the respective ring-shaped element irrespective of the elastic deformation of the adjacent ring-shaped element; the enveloping is achieved due to the multiplicity of the supports, and when the carrier passes the pipe section having a defect of geometry, the support envelops the defect: at the beginning of movement the front part of the support is closer to the pipeline axis than the rear part and at the end of the enveloping the rear part of the support is closer to the pipeline axis than the front one. In so doing the next supports along the perimeter about the carrier axis above the non-defective pipeline sections do not make a similar enveloping movement, and the gap between the sensors installed in these elements and the internal surface of the pipeline practically does not change. The functions of applying the pressure on the sensors and enveloping the obstacles are different, the pressure provided by the ring elements can be high enough and does not effect the capability of enveloping the obstacles in the above way.

In the sixth embodiment of the claimed group of inventions: the carrier includes at least four ring elements; in the preferable embodiment the ring elements are made as corrugated elastic (polymeric) rings whose features are specified below after the description of all embodiments of the group of inventions.

The setting places for sensors are made as holes or cuts or depressions and form rows oriented at an angle of 0 to 30 degrees to the carrier axis along the spiral line about the carrier axis, the setting places for sensors being made in the convex parts of the supports.

In the optional embodiments to be realized: the ring-shaped element is inscribed into a cylinder whose diameter is less than the internal diameter of the pipeline but at least equal to a half the diameter of the cylinder, in which the carrier is inscribed; the ring-shaped element includes rigid links, as well as elastic and/or pivot joints between the links; the ring-shaped element includes rigid and/or elastic links and pivot joints between the links.

The choice of the design of the ring elements is determined by the standard size of the carrier and by the type of the tested pipeline: at a large diameter rigid couplings and pivot joints are preferable, at a smaller diameter elastic links and couplings are preferable.

The length of the support between the neighboring ring-shaped elements along the carrier axis does not exceed 0.4 diameter of the cylinder, in which the carrier is inscribed, the angular width of the support relative to the carrier axis in a plane normal to the carrier axis does not exceed 60 degrees, an increase of support width above said limit weakens the capability of enveloping the defects of geometry.

In the preferable embodiment of the sixth embodiment of the claimed group of inventions the sensor carrier also includes skids installed on the supports in compliance with the above-described second embodiment, and/or a housing, on which the ring elements are installed, in compliance with the above-described third embodiment, and/or the supports are made as rows of grouped elements in compliance with the above-described fourth embodiment.

In each of the described embodiments of a group of inventions the setting places for sensors form rows oriented on a spiral (helical) line about the carrier axis, preferably at an angle of 0 to 30 degrees to the carrier axis to provide overlapping the entire perimeter in the cross section of the pipeline by the sensors, the external surfaces of the rings (ring elements, ring-shaped supports) pass near to the internal surface of the pipeline and are inscribed into a cylinder concentric to the pipeline.

In each embodiment the corrugated elastic rings in preferable execution are characterized by the following features.

The angle between the direction forming a corrugation on the ring and the direction of ring axis is within 0 to 45 degrees, the corrugations of each ring are displaced relative to the corrugations of the adjacent rings by an angle about the ring axis, the internal surfaces of the corrugations form a cylinder whose diameter is equal to 0.3-0.9 diameter of the cylinder, into which the ring is inscribed, an amount of convex parts of the corrugation on one ring is equal to 0.3-5.0 said diameter expressed in inches, the rings are rigidly or elastically connected to the adjacent rings, at least some of the rings are fixed together by rods or slats, which are rigid or elastic.

In the preferable embodiment the rings are made of an elastic polymeric material, an average thickness of the ring (average by the integrated thickness in a plane normal to ring axis along the perimeter) is equal to 0.01-0.2 diameter of the cylinder, into which said ring is inscribed. An average width of the ring (by the integrated width in the direction of ring axis along the ring perimeter) is not less than 0.01 and not more than 0.4 diameter of the cylinder, into which said ring is inscribed.

The corrugations form rings springing in the ring plane, the rows of sensors along the helical line provide overlapping of the whole perimeter in the cross section of the pipeline by the sensors. At a smaller diameter of the cylinder the area of compression of the ring is limited when the support passes the defect of the pipe geometry; at a larger internal diameter of the ring or a small amount of the convex parts of the corrugations the spring properties of the rings are weakened; at an amount of corrugations greater than that mentioned above the area of compression between the folds of the corrugations is limited.

The given range has been found optimal for uniformly pressing the sensors to the internal surface of the pipeline taking into account their weight, on the one hand, and the capability of the spring to deformation when passing the dents and other defects of geometry, on the other hand.

The angle between the ring axis direction and the pipeline axis direction is in a range of 0 to 30 degrees, therefore, the rings connected in series form a spiral (helical line) about the carrier axis or (in the preferable embodiment) the rings are installed along a single axis, said axes coinciding with the pipeline axis.

The sensors can be fixed as follows: (1) the setting place for the monitoring sensor is made in the form of a sleeve fixed in the sleeve support and having a threaded portion protruding above the support and used for fixing the sensor by means of a coupling nut. The sensors are installed in the sleeves and are fixed by coupling nuts. (2) the setting places for the sensor are made as a hole whose internal surface of each hole (near the edge) has a slot for a locking ring. The sensors are immersed into said holes and secured by the locking rings.

The additional technical result common for all embodiments of the claimed group of inventions is attained by an independent part of the mechanism for achieving said basic technical result consists in reduction of the amount of sensors whose orientation relative to an internal surface of the pipeline varies when the carrier passes the defect of geometry in the cross section of the pipeline due to independent attachment and orientation of the sensors relative to the adjacent sensors at the site of defect in the pipe geometry.

BRIEF DESCRIPTION OF THE DRAWINGS

These and other features, aspects, and advantages of the present invention will become better understood upon consideration of the following detailed description, appended claims, and drawings where:

DETAILED DESCRIPTION OF THE INVENTION

As a result of solving the technical problem of increasing the efficiency of the flaw detection of long distance pipelines, in-tube flaw detectors (in-tube inspection scrapers) for testing oil pipelines, gas pipelines and condensate pipelines with a nominal diameter from 10" to 56" have been developed. As a rule, the in-tube inspection scraper includes one or several sections forming explosion-proof shells and a sensor carrier. The shells accommodate a power supply and electronic equipment for measurements, processing and storage of the obtained measurement data in an onboard computer controlling the scraper operation during its travel inside the pipeline. The scraper housing has polyurethane sleeves centering the inspection scraper inside the pipeline and providing its movement by a flow of fluid conveyed through the pipeline, as well as odometers metering the distance passed inside the pipeline. The information on the length of the passed way measured by the odometers with binding to the measured diagnostic parameters is recorded in the memory of the onboard computer and allows one to perform processing of the recorded data to determine the location of the defects in the pipeline and, respectively, the place of subsequent excavation and repair of the pipeline.

Figure 1:
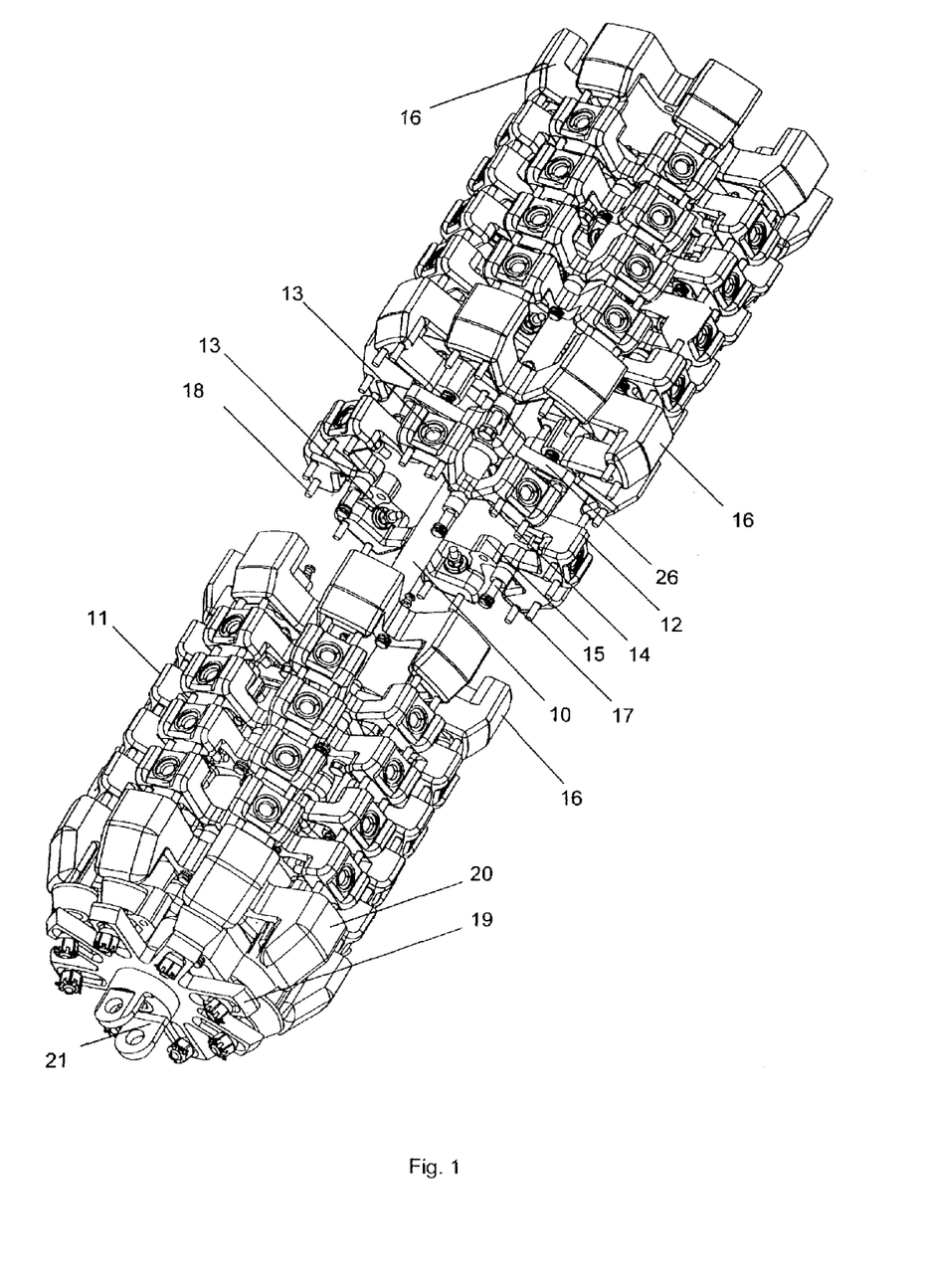
FIG. 1 illustrates a sensor carrier with ring-shaped sensor supports in one of practical embodiments.
Figure 2:
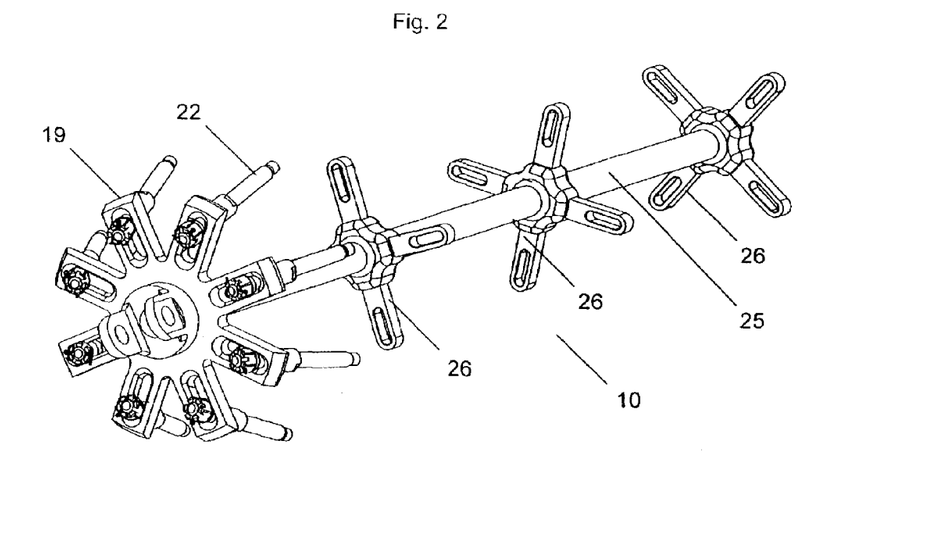
FIG. 2 illustrates the sensor carrier housing capable of bending.
Figure 3:
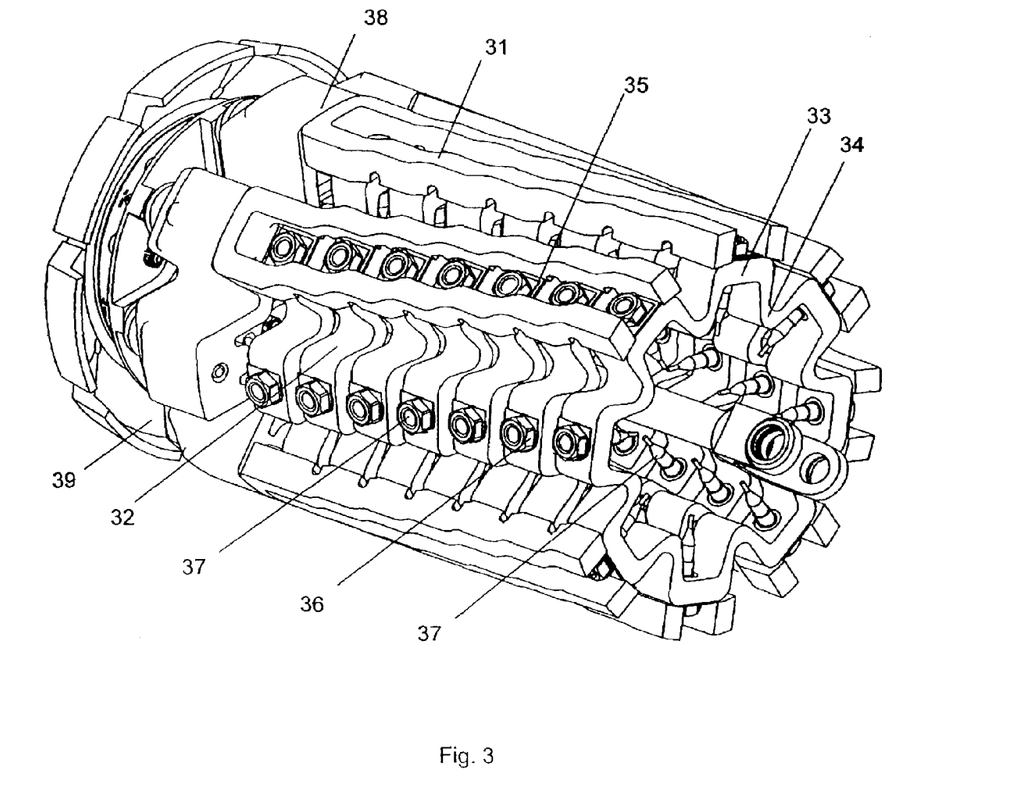
FIG. 3 illustrates a section of the sensor carrier with skids in one of practical embodiments.
Figure 4:
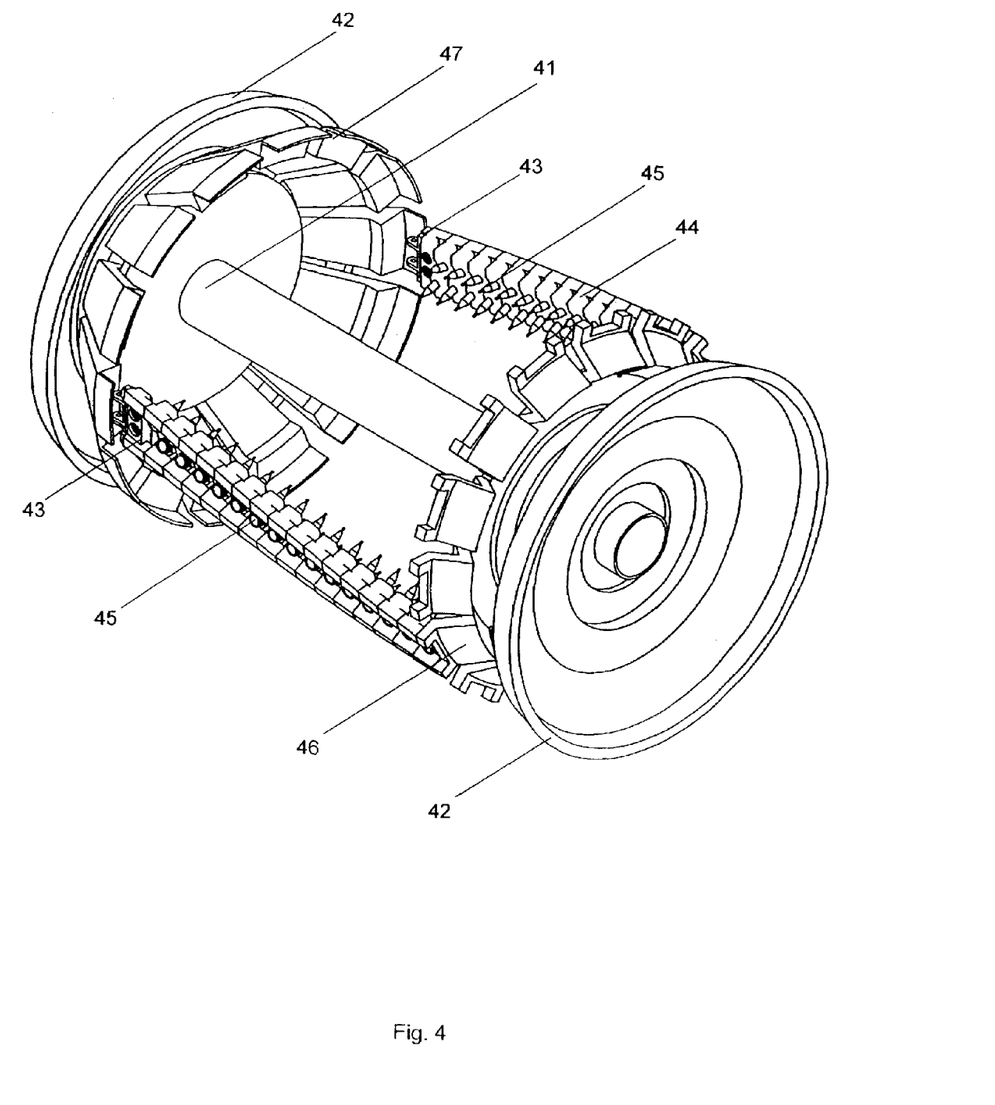
FIG. 4 illustrates a sensor carrier with rows of grouped elements with sensors in one of practical embodiments.
Figure 5:
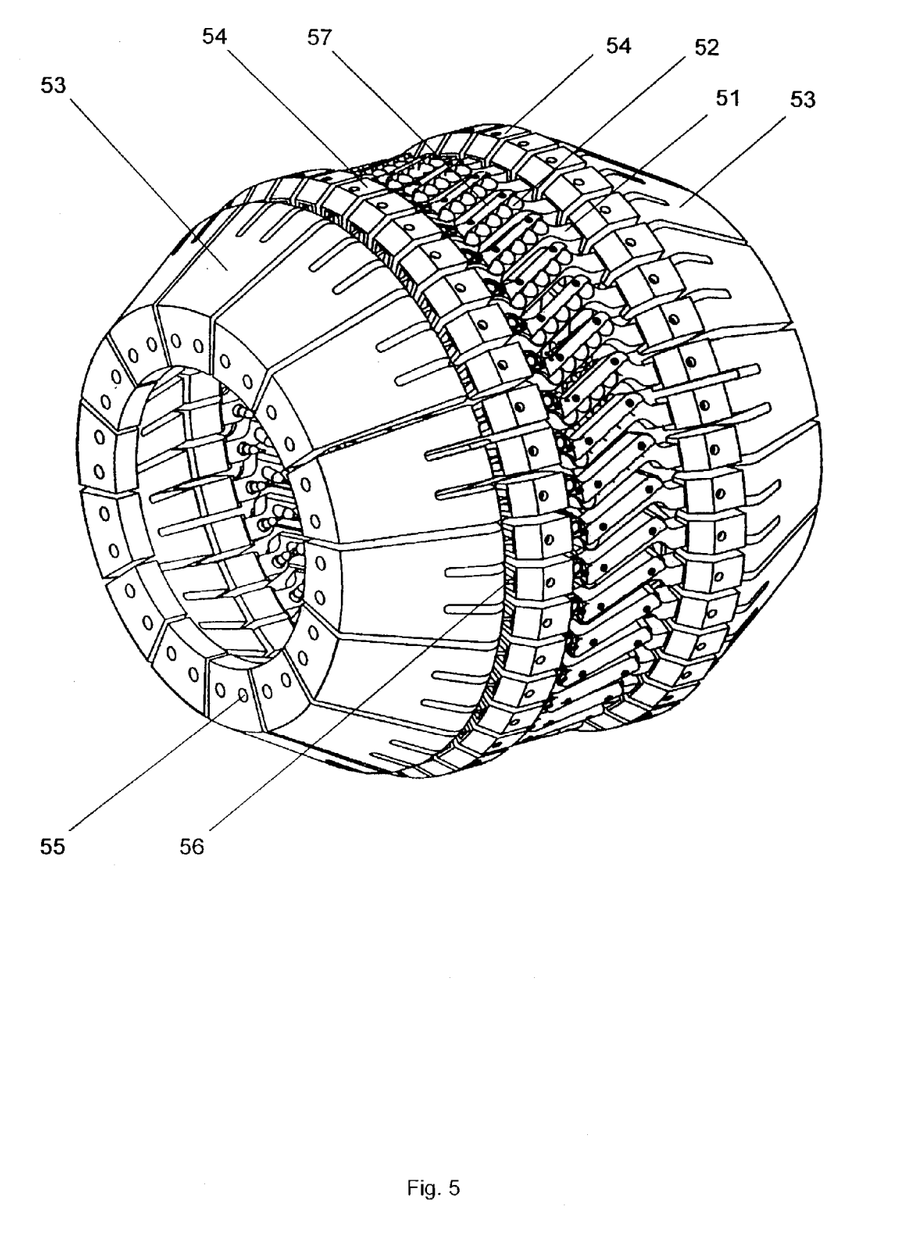
FIG. 5 illustrates a section of the sensor carrier with belts of sensor supports in one of practical embodiments.
Figure 6:
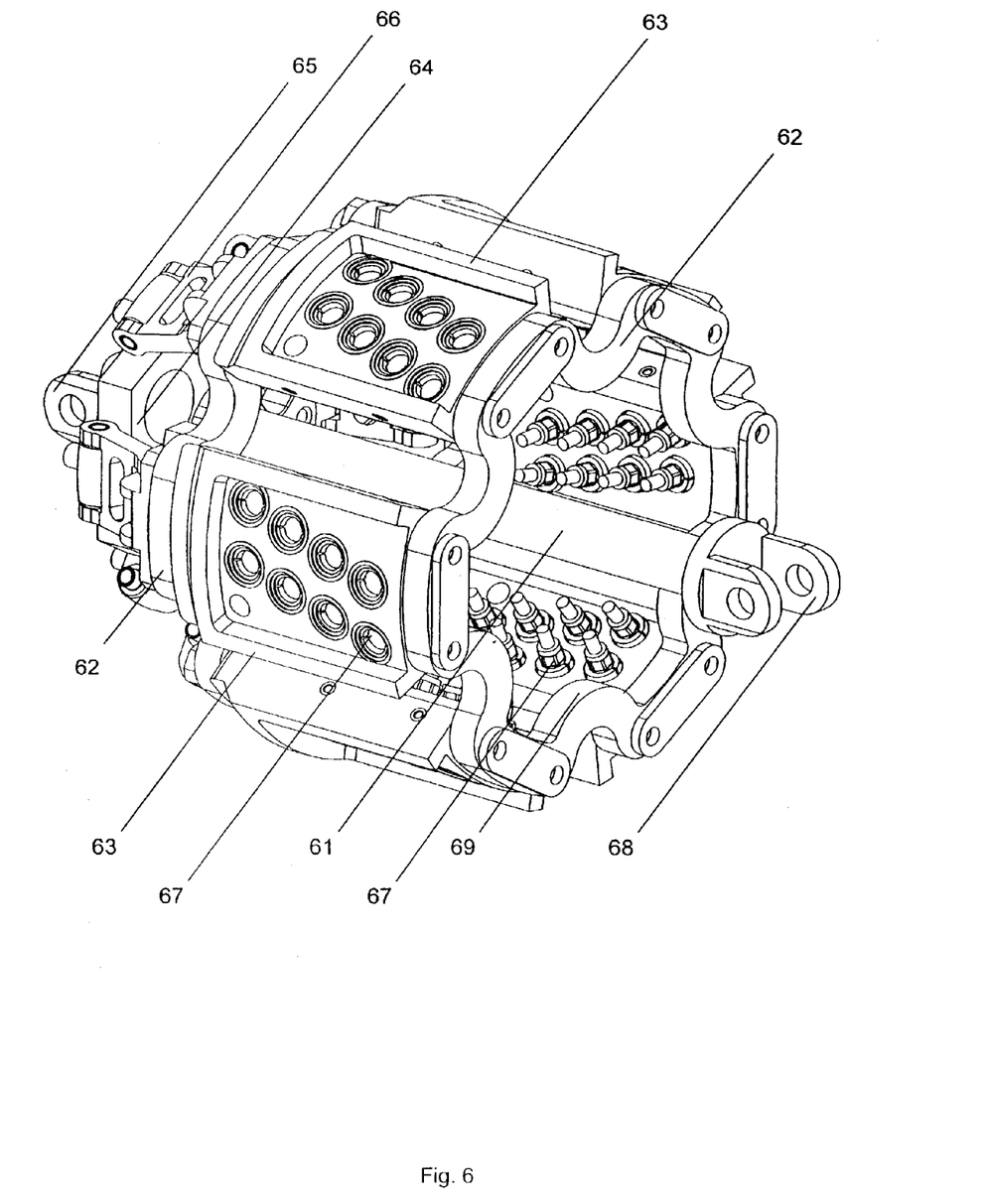
FIG. 6 illustrates a section of the sensor carrier with sensor supports installed on ring elements in one of practical embodiments.

FIGS. 1-6 illustrate the embodiments of the sensors carriers characterized by the features of the claimed group of inventions; the sensor carrier shown in FIG. 1 with a housing shown in FIG. 2 is characterized by the features on the first and third embodiments of the claimed group of inventions; the sensor carrier whose cross section is shown in FIG. 3 is characterized by the features according to the first and second embodiments of the claimed group of inventions; the sensor carrier shown in FIG. 4 is characterized by the features according to the fourth embodiment of the claimed group of inventions; the sensor carrier shown in FIG. 5 is characterized by the features according to the fifth embodiment of the claimed group of inventions; and the sensor carrier shown in FIG. 6 is characterized by the features according to the sixth embodiment of the claimed group of inventions.

The sensor support in one of the embodiments shown in FIGS. 1-2 (for better understanding the three ring-shaped supports of the medium group are not shown) comprises a housing 10 and twelve ring-shaped supports 11 in the form of corrugated elastic rings of an elastic polymeric material with eight convex corrugations 12, and eight setting places for sensors 13 in the convex parts of corrugations on each ring, and 8 concave sections of corrugations 14; the corrugations of each ring are displaced relative to the corrugations of the adjacent rings through an angle of approximately 4 degrees about the axis of the rings, the internal surfaces of the corrugations 15 form a cylinder whose diameter is equal to about 60% of the diameter of the cylinder, into which the ring is inscribed. The distance between the adjacent rings is equal to about 3% of the diameter of the cylinder, into which the carrier is inscribed, the width of the rings being equal to about 10-15% of said diameter. Eight convex parts of the corrugations on one ring make about 0.8 said diameter expressed in inches, the ring thickness being equal to about 0.07 said diameter.

The rings are grouped in 3 groups by 4 rings. Installed in the rear part of the carrier between the groups of elements on the carrier housing are fluted rings 16 of a higher diameter (relative to rings 11 diameter), which are inscribed into a cylinder whose diameter exceeds the diameter of the cylinder formed by rings with sensors and is not less than the internal diameter of the pipeline being tested. In each groups the rings are fastened together and coupled with the elements of a higher diameter by rigid fastening members 17, the ring elements are arranged along the pipeline axis, rigid elements 18 being mold in the ring and rest on the adjacent rings.

Mounted in the front part of the carrier are a metal flange 19 and a conical element 20, the latter being installed between the flange and the rings. The conical element and the rings are inscribed into a cylinder with a diameter of about 10", the rings with setting places for sensors are inscribed into a cylinder with a diameter of about 9" that is equal to about 90% of the internal diameter of the pipeline, for which the carrier of such a design is intended. The flange has a fastening member 21 for fixing the flange to the hardware part of the in-tube inspection scraper. Near the flange the ring is connected to a flange 19 by rigid rods 22 (FIG. 2) extending through the conical element 20, the axes of the rods 22 forming a conical surface coaxial with the pipeline. The conical element forms a corrugated conical sleeve, the direction of the corrugations coinciding with the carrier axis direction. The rings and conical element are made of polyurethane. In the embodiment shown in FIG. 1 the monitoring sensors are ultrasonic devices fixed in the setting places with the help of locking rings.

The ring elements are mounted on the housing 10 (FIG. 2) which is capable of bending. The housing includes an elastic polyurethane rod 25 of a round cross section with a core made as a metal cable. Attached to the core are three cross-like metal flanges 26 (FIGS. 1, 2), connected to the ring elements 16 of a higher diameter and adjacent rings with sensors 11. A flange 19 is secured on the rod in the front part of the housing (FIGS. 1, 2). The length of the fixed part of the housing in its nose part along the carrier axis is about 0.15 diameter of the cylinder, into which the carrier is inscribed. The lower limit of allowable bending radius of the carrier axis is about 1.5 diameters the cylinder.

In possible embodiments of the invention the housing includes three hingedly interconnected elastic rods corresponding to three groups of ring elements, each element carrying four ring elements with setting holes for the sensors.

FIG. 3 illustrates a section of the sensor carrier in another embodiment (for simplicity one of the skids on the support is not shown). The sensor carrier includes skids 31 capable of sliding along the internal surface of the pipeline, kinematically connected elements in the form of corrugated elastic ring-shaped elements 32 with eight convexities of corrugations 33 (and eight concavities of corrugations 34 respectively), as well as eight setting places for sensors in the convex parts of the corrugations 33 made as through holes. The ring elements are installed along an axis coinciding with the pipeline axis. Each skid 31 is fixed on seven ring elements 32 with the help clamps 35 mold in the skid and forms a gasket between the ring elements and the internal surface of the pipeline. The clamps have a hole for a sensor, and a coupling nut 36 secures the sensor 37 and presses the skid 31 to the ring element 32. Each ring element is inscribed into a cylinder with a diameter of about 11" and this is a little smaller than the internal diameter of the pipeline (12") to be tested by the carrier. The angle between the skid direction and the carrier axis direction is equal to about 10 degrees, the skids are oriented along a curve forming a helical line about the carrier axis.

Eight convex parts of the corrugations on one ring element make about 0.8 its diameter expressed in inches, the ring element width is equal to about 0.05-0.10 its diameter, the ring element thickness is equal to about 0.07 its diameter, the skid thickness is about 0.1 diameter of the cylinder, into which the ring is inscribed. The ultrasonic sensors 37 are inscribed into the cylinder whose diameter exceeds the diameter of the cylinder, into which the ring elements are inscribed.

Installed at the front part of the support are a metal flange and a conical element 38, the conical element being placed between the flange and the ring elements. The conical element is inscribed into a cylinder with a diameter of about 12", the ring elements with setting places for sensors are inscribed into a cylinder with a diameter of about 11", i.e. about 90% of the internal diameter of the pipeline. Fixed to the flange is fastening member for the hardware of the in-tube inspection scraper. The skids are connected to the flange by rigid rods extending through the conical element 38, the axes of the rods forming a conical surface coaxial to the pipeline. The conical element forms a corrugated conical sleeve, the direction of the corrugations coincides with the carrier axis direction. The ring and conical elements are made of polyurethane.

Installed at the front part of the support are elastic fins 39 extending from the axis in a radial direction. The peripheral edges of the fins are subjected to elastic deformation in a plane extending through the carrier axis. Fins are made of polyurethane and are installed in such a manner that the setting places for sensors are projected on the fins in a plane normal to the carrier axis, said fins forming an elastic coupling with the carrier at the points of their attachment on the carrier housing. In the embodiment shown in FIG. 3 the monitoring sensors are ultrasonic and the lenses of ultrasonic sensors form a surface whose diameter exceeds the diameter of the surface formed by the convexities of the ring elements. The carrier housing includes several rods hingedly connected to each other. In the embodiment shown in FIG. 3 the monitoring sensors are ultrasonic and fixed in the sleeves with the help of coupling nuts.

FIG. 4 illustrates a sensor carrier of another design (for simplicity, only two rows of grouped elements with sensors are shown in the drawing, the other rows being installed similarly). The sensor carrier includes a housing 41 with sleeves 42 installed therein, rows 43 of elements 44 pressed to each other and having setting places for sensors 45. Each row is strapped with a metal cable and is oriented along a helical line about the carrier axis forming an angle of about 10 degrees with the carrier axis. The elements of the row form movable (hinged or elastic) connections with the adjacent elements of the row at the joints. The surfaces of the elements contacting the internal surface of the pipeline form a cylinder coaxial with the pipeline. Each row at a front part of the carrier is connected to the housing through a hinge, at the rear part of the support the row is connected to the elastic supporting members 46 fixed to the housing 41.

The grouped elements of each row have centering members for positioning relative to the next grouped elements in the form of projections and slots so that the projections of one element enter the slots of the adjacent element, the projections being formed by metal elements, molded in the grouped elements. The setting place for the monitoring sensor is made as a sleeve fixed in an elastic element for the sensor with a threaded sleeve part protruding above the elastic element and used for a coupling nut. Installed at the front part of the support are elastic fins 47 extending from the axis in a radial direction. The peripheral edges of the fins are subjected to elastic deformation in a plane extending through the carrier axis. The fins are installed in such a manner that the setting places for sensors are projected on the fins in a plane normal to the carrier axis. The fins form an elastic coupling with the carrier at places of their attachment on the support. In the embodiment shown in FIG. 4 the monitoring sensors are ultrasonic. The sleeves 42, grouped elements 44, elastic elements 46 and fins 47 are made of polyurethane. In the embodiment shown in FIG. 4 the monitoring sensors are ultrasonic and fixed in the sleeves by means of coupling nuts.

FIG. 5 illustrates another embodiment of the sensor carrier (for better understanding, the carrier section installed on the housing is shown). The carrier includes a belt of supports 51 with setting places for sensors 52 and two belts of radially extending levers 53 as sectors of sleeves installed on both sides of the belt of supports towards each other. The edges of the supports of the belt are secured at both sides with the peripheral parts of the respective sectors of sleeves, the supports are provided with gaskets 54 capable of sliding along the internal surface of the pipeline, the gaskets 54 forming pairs on different sides of the setting places. The carrier includes a housing with flanges, the sectors 53 of the sleeve are fixed on the flanges with the help of bolts (pins) extending through holes 55 in levers (sectors) 53. Each sector of the sleeve is connected to three supports. The flange has springing elements resting on the internal part of the sectors and extending them. The sectors 53 of the sleeves and the gaskets 54 are made of polyurethane, an average thickness of the sector is equal to 0.06 diameter of the cylinder, into which the carrier is inscribed, in peripheral parts of the sleeves having integrated fastening members 56 for the supports 51 of the belt. The angular width of sleeve sector in its peripheral part is equal to about 26 degrees, the length of the sector part capable of bending is equal to about 0.25 diameter of the cylinder, into which the carrier is inscribed. In embodiment shown in FIG. 5, the monitoring sensors are ultrasonic and fixed in the sleeves by means of coupling nuts, pressed to supports 51 by covers 57.

FIG. 6 illustrates still another embodiment of the sensor carrier. The carrier includes a housing 61, corrugated elastic rings 62, sensor support 63 secured on rings 62. The housing 61 has a flange 64 having a fastening member 65 to fix the carrier to the hardware part of the in-tube inspection scraper, the front ring 62 being connected to a flange 64 through a hinged mechanism 66. One section of the carrier is hingedly connected to the others sections through an element 68 of the housings 61. The length of the supports along the pipeline axis is equal to about 0.4 diameter of the cylinder, into which the carrier is inscribed, the width of the rings is equal to about 0.05 diameter of the cylinder, into which the ring is inscribed, the ring thickness is equal to about 0.07 said diameter. In the embodiment shown in FIG. 6 the monitoring sensors 67 are ultrasonic and fixed in the setting places with the help of locking rings.

The internal surfaces of the corrugations 69 form a cylinder whose diameter is equal to about 60% of the diameter of the cylinder, into which the rings are inscribed. Six convex parts of the corrugations on one ring make about 0.6 its diameter expressed in inches.

In any described embodiment the sensor carrier can be hingedly connected to the hardware of the inspection scraper.

The device operates as follows:

The sensors are installed in the carrier and connected to the hardware sections of the inspection scraper. The scraper is put in the pipeline and a product (oil, gas, oil product) is forced through the pipeline. During the travel of the inspection scraper inside the pipeline the diagnostic parameters describing the pipeline conditions are measured.

The ultrasonic monitoring sensors periodically send ultrasonic pulses. Having emitted the ultrasonic pulse, the ultrasonic sensors switch over to reception of the reflected pulses. The obtained data on the temporary intervals corresponding to the time of run of the ultrasonic pulses and (if necessary) the pulse amplitudes are digitized, converted and written in a storage device of the onboard computer.

During the magnetic control of pipeline some area of the pipe wall is magnetized and the magnetic field sensors measure the magnetic field components near the magnetized area of pipe wall. The measurement of the magnetic field is made by periodically interrogating the magnetic field sensors. The presence of cracks or defects associated with a loss of metal (corrosion, scratches) results in a change of magnitude and character of the magnetic induction distribution.

The flaw detection of a pipeline can also be performed by means of sensors of the other type (magneto-optical, optical, electromagnetic-acoustic, pipe profile detectors, for example, by means of periodic measurement of the angle of turn of the levers pressed to the internal surface of the pipeline, etc.), amplification of the pulses from the sensors, digitization of amplitudes and recording the digital data in a storage device.

Having completed the inspection of the given site of the pipeline the scraper (defectoscope) is removed from the pipeline and the data recorded during the diagnostic travel are transferred to an independent computer.

The subsequent analysis of the written data allows one to identify the defects on the pipe wall and to determine their location on the pipeline with the purpose of subsequent repair of defective pipeline sections.

The carrier allows one to increase the efficiency of the flaw detection in pipelines having defects of geometry in the cross section. This is provided due to multiplicity of elements (supports) with setting places for sensors and distribution of the functions of pressing the sensors to the internal surface of the pipeline and enveloping the defects of geometry in the pipe cross section, a decrease of the change of the gap between the sensor and the pipe wall. The invention makes it possible to reduce the amount of sensors whose orientation relative to the internal surface of the pipeline varies when the support is passing a defect of geometry in the cross section of the pipeline.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. An in-tube inspection scraper for use in a pipeline having a defect of geometry, the in-tube inspection scraper comprising:
   a sensor carrier having a carrier axis of symmetry, the sensor carrier comprising:
   a housing, and a set of interconnected corrugated elastic rings having convex corrugations with a set of sensors installed in the convex corrugations,
   said corrugated elastic rings being kinematically connected to the housing,
   external surfaces of said corrugated elastic rings extending along a cylindrical surface corresponding to an internal surface of the pipeline,
   the convex corrugations being subjected to an elastic force acting in the radial direction from the carrier axis of symmetry provided by the corrugated elastic rings when the scraper is in use in the pipeline, wherein when the carrier travels through a pipe section having the defect of geometry the rings with sensors both in a zone of pipe deformation and in a non-deformed zone are pressed to the internal surface of the pipeline,
   wherein there is a distance between adjacent corrugated elastic rings.

2. The scraper according to claim 1, wherein:
   the convex corrugations of each ring are displaced relative to the convex corrugations of adjacent rings by an angle about the carrier axis of symmetry, and
   at least some of the rings are fastened together by means of rods or slats.

3. The scraper according to claim 1, wherein:
   the corrugated elastic rings are made of a polymeric material,
   an average thickness of each of the corrugated elastic rings is equal to 0.01-0.2 times a diameter of an imaginary cylinder into which each of the corrugated elastic rings is inscribed, and
   the average width of each of the corrugated elastic rings is not less than 0.01 and not more than 0.4 said diameter of the imaginary cylinder.

4. The scraper according to claim 1, wherein:
   the carrier includes supporting elements connected to the corrugated elastic rings, the corrugated elastic rings being disposed between said supporting elements, and the supporting elements being made in the form of corrugated elastic rings, and/or elastic sleeves, and/or elastic disks.

5. The scraper according to claim 1, wherein:
   the carrier includes at least four corrugated elastic rings,
   the distance between adjacent corrugated elastic rings does not exceed half of a diameter of an imaginary cylinder into which the carrier is inscribed,
   the width of each corrugated elastic ring is less than said diameter and does not exceed 0.25 said diameter, and
   the angle between an axis of symmetry of each corrugated elastic ring and the direction of an axis of symmetry of the pipeline in which the carrier is placed is within 0 to 30 degrees.

6. The scraper according to claim 1, wherein:
   each of the corrugated elastic rings is installed along a single axis coinciding with a pipeline axis of symmetry, and
   at least some of the corrugated elastic rings are fastened together by means of rods or slats.

7. The scraper according to claim 1, wherein:
   said sensors form rows oriented at an angle of 0 to 30 degrees to the carrier axis of symmetry along an imaginary spiral line about said carrier axis of symmetry.

8. The scraper according to claim 1, wherein:
   the housing has an axis of symmetry coinciding with a pipeline axis of symmetry, the housing being capable of bending.

9. The scraper according to claim 1, wherein:
   the housing includes rigid links, as well as elastic and/or pivot joints between the links.

10. The scraper according to claim 1, wherein:
    the housing includes rigid and/or elastic links and pivot joints between the links, the elastic links being made of a polymeric material.

11. The scraper according to claim 1, wherein:
    the housing is made as a braid, or a cable, or a hose, or bellows, or a spring or a strip.

12. The scraper according to claim 1, wherein:
    the carrier includes at least four said corrugated elastic rings.

13. An in-tube inspection scraper for use in a pipeline having a defect of geometry, the in-tube inspection scraper comprising:
    a sensor carrier having a carrier axis of symmetry, the sensor carrier comprising:
    a housing, and a set of interconnected corrugated elastic rings having convex corrugations with a set of sensors installed in the convex corrugations, said corrugated elastic rings being kinematically connected to the housing, external surfaces of said corrugated elastic rings extending along a cylindrical surface corresponding to an internal surface of the pipeline, the convex corrugations being subjected to an elastic force acting in the radial direction from the carrier axis of symmetry provided by the corrugated elastic rings when the scraper is in use in the pipeline, wherein when the carrier travels through a pipe section having the defect of geometry the rings with sensors both in a zone of pipe deformation and in a non-deformed zone are pressed to the internal surface of the pipeline, wherein the convex corrugations of each ring are displaced relative to the convex corrugations of adjacent rings by an angle about the carrier axis of symmetry, and at least some of the rings are fastened together by means of rods or slats.

14. The scraper according to claim 13, wherein:
the corrugated elastic rings are made of a polymeric material,
an average thickness of each of the corrugated elastic rings is equal to 0.01-0.2 times a diameter of an imaginary cylinder into which each of the corrugated elastic rings is inscribed, and
the average width of each of the corrugated elastic rings is not less than 0.01 and not more than 0.4 said diameter of the imaginary cylinder.

15. The scraper according to claim 13, wherein:
the carrier includes supporting elements connected to the corrugated elastic rings, the corrugated elastic rings being disposed between said supporting elements, and the supporting elements being made in the form of corrugated elastic rings, and/or elastic sleeves, and/or elastic disks.

16. The scraper according to claim 13, wherein:
the carrier includes at least four corrugated elastic rings,
the distance between adjacent corrugated elastic rings does not exceed half of a diameter of an imaginary cylinder into which the carrier is inscribed,
the width of each corrugated elastic ring is less than said diameter and does not exceed 0.25 said diameter, and
the angle between an axis of symmetry of each corrugated elastic ring and the direction of an axis of symmetry of the pipeline in which the carrier is placed is within 0 to 30 degrees.

17. The scraper according to claim 13, wherein:
said sensors form rows oriented at an angle of 0 to 30 degrees to the carrier axis of symmetry along an imaginary spiral line about said carrier axis of symmetry.

18. The scraper according to claim 13, wherein:
the housing has an axis of symmetry coinciding with a pipeline axis of symmetry,
the housing being capable of bending.

19. The scraper according to claim 13, wherein:
the housing includes rigid links, as well as elastic and/or pivot joints between the links.

20. The scraper according to claim 13, wherein:
the housing includes rigid and/or elastic links and pivot joints between the links, the elastic links being made of a polymeric material.

21. The scraper according to claim 13, wherein:
the housing is made as a braid, or a cable, or a hose, or bellows, or a spring or a strip.

22. The scraper according to claim 13, wherein:
the carrier includes at least four said corrugated elastic rings.

23. An in-tube inspection scraper for use in a pipeline having a defect of geometry, the in-tube inspection scraper comprising:
a sensor carrier having a carrier axis of symmetry, the sensor carrier comprising:
a housing, and a set of interconnected corrugated elastic rings having convex corrugations with a set of sensors installed in the convex corrugations,
said corrugated elastic rings being kinematically connected to the housing,
external surfaces of said corrugated elastic rings extending along a cylindrical surface corresponding to an internal surface of the pipeline,
the convex corrugations being subjected to an elastic force acting in the radial direction from the carrier axis of symmetry provided by the corrugated elastic rings when the scraper is in use in the pipeline, wherein when the carrier travels through a pipe section having the defect of geometry the rings with sensors both in a zone of pipe deformation and in a non-deformed zone are pressed to the internal surface of the pipeline,
wherein each of the corrugated elastic rings is installed along a single axis coinciding with a pipeline axis of symmetry, and
at least some of the corrugated elastic rings are fastened together by means of rods or slats.

24. The scraper according to claim 23, wherein:
the corrugated elastic rings are made of a polymeric material,
an average thickness of each of the corrugated elastic rings is equal to 0.01-0.2 times a diameter of an imaginary cylinder into which each of the corrugated elastic rings is inscribed, and
the average width of each of the corrugated elastic rings is not less than 0.01 and not more than 0.4 said diameter of the imaginary cylinder.

25. The scraper according to claim 23, wherein:
the carrier includes supporting elements connected to the corrugated elastic rings, the corrugated elastic rings being disposed between said supporting elements, and the supporting elements being made in the form of corrugated elastic rings, and/or elastic sleeves, and/or elastic disks.

26. The scraper according to claim 23, wherein:
the carrier includes at least four corrugated elastic rings,
the distance between adjacent corrugated elastic rings does not exceed half of a diameter of an imaginary cylinder into which the carrier is inscribed,
the width of each corrugated elastic ring is less than said diameter and does not exceed 0.25 said diameter, and
the angle between an axis of symmetry of each corrugated elastic ring and the direction of an axis of symmetry of the pipeline in which the carrier is placed is within 0 to 30 degrees.

27. The scraper according to claim 23, wherein:
said sensors form rows oriented at an angle of 0 to 30 degrees to the carrier axis of symmetry along an imaginary spiral line about said carrier axis of symmetry.

28. The scraper according to claim 23, wherein:
the housing has an axis of symmetry coinciding with a pipeline axis of symmetry,
the housing being capable of bending.

29. The scraper according to claim 23, wherein:
the housing includes rigid links, as well as elastic and/or pivot joints between the links.

30. The scraper according to claim 23, wherein:
the housing includes rigid and/or elastic links and pivot joints between the links, the elastic links being made of a polymeric material.

31. The scraper according to claim 23, wherein:
the housing is made as a braid, or a cable, or a hose, or bellows, or a spring or a strip.

32. The scraper according to claim 23, wherein:
the carrier includes at least four said corrugated elastic rings.

* * * * *